Figure 1:
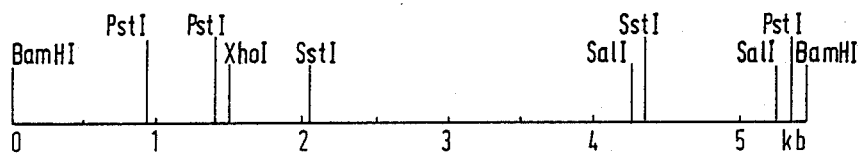

United States Patent [19]

Muth et al.

[11] Patent Number: 4,963,496
[45] Date of Patent: Oct. 16, 1990

[54] COLOR MARKER IN STREPTOMYCETES PLASMIDS

[75] Inventors: Günter Muth; Wolfgang Wohlleben; Alfred Pühler, all of Bielefeld; Gerhard Wöhner, Flörsheim am Main; Rüdiger Marquardt, Frankfurt am Main, all of Fed. Rep. of Germany

[73] Assignee: Hoechst Aktiengesellschaft, Frankfurt am Main, Fed. Rep. of Germany

[21] Appl. No.: 83,806

[22] Filed: Aug. 11, 1987

[30] Foreign Application Priority Data

Aug. 13, 1986 [DE] Fed. Rep. of Germany ....... 3627405

[51] Int. Cl.$^5$ ...................... C12N 15/00; C12N 1/20; C12P 21/00
[52] U.S. Cl. ................................... 435/320; 435/69.1; 435/71.2; 435/252.35; 435/172.3; 935/29; 935/75
[58] Field of Search ............ 435/68, 91, 172.1, 172.3, 435/320, 252.3, 252.31–252.35, 886, 69.1, 71.2, 183; 536/27; 935/11, 14, 29, 75

[56] References Cited

U.S. PATENT DOCUMENTS 4,828,998 5/1989 Wöhner et al. .................... 435/886

FOREIGN PATENT DOCUMENTS 0154430 11/1985 European Pat. Off. ......... 435/172.3

OTHER PUBLICATIONS

Habermehl et al., "Amylocyanin, the Blue Pigment of *Streptomyces coelicolor*", Chem. Abst., vol. 86, 185565e (1977).
Chater et al; Top. Microbiol. Immunoll 96: 69–95 (1982).
Habermehl et al., "Isolation, Separation and Structure of the Blue Bacterial Pigment . . .", Chem. Abst., vol. 88, 47257w (1978).
Katz, E. et al., "Cloning and Expression of the Tyrosinase Gene from Streptomyces Antibioticus in *Streptomyces lividans*," J. Gen'l Microbiology 129: 2703–14 (1983).

*Primary Examiner*—James Martinell
*Attorney, Agent, or Firm*—Finnegan, Henderson, Farabow, Garrett, and Dunner

[57] ABSTRACT

Intensely blue-black colonies are obtained from *Streptomyces coelicolor* DSM 3030 by total digestion of the total DNA, cloning into a suitable vector, and transformation of a streptomycetes recipient strain. Re-isolation of the plasmid DNA and cutting with BamHI results in a 5.5 kb fragment on which the gene for the coloring agent is located. This gene is suitable as marker, in particular as inactivation marker, in Streptomycetes.

6 Claims, 2 Drawing Sheets

COLOR MARKER IN STREPTOMYCETES PLASMIDS

The mel gene is presently known as color marker for cloning into Streptomycetes (E. Katz et al., J. Gen. Microbiol. 129 (1983) 2703) since it codes for tyrosinase and thus—via intermediates—is responsible for producing the coloring agent melanin. This gene is contained in, for example, the commercially available plasmid pIJ702, which can be obtained from the John Innes Foundation, Norwich, England, and is described, for example in D. A. Hopwood et al., Genetic Manipulation of Streptomyces—A Laboratory Manual, The John Innes Foundation, 1985, pages 292 et seq. However, this marker has the disadvantage that the coloring agent which is formed readily diffuses into the surrounding medium.

A coloring marker which is expressed in Streptomycetes and brings about an intense deep blue or black coloration in the medium, but which diffuses only slightly in solid media, has now been found. By use of this as inactivation marker even very rare events can readily be detected.

Hence the invention relates to a gene which codes for a blue coloring agent in Streptomycetes and can be obtained from the total DNA of *Streptomyces coelicolor* DSM 3030 by cutting with BamHI, isolation of a fragment about 5.5 kb in size, and selection for production of coloring agent. This gene is characterized in detail by the restriction map shown in FIG. 1. The starting strain *S. coelicolor* DSM 3030 is mentioned in the European Patent Application with the publication number 0 181 562 as producer of a bacteria-lysing enzyme.

The invention furthermore relates to the use of the gene according to the invention as marker, in particular as inactivation marker, in Streptomycetes plasmids.

Further aspects of the invention and its preferred embodiments are evident from the description which follows and from the patent claims.

In order to isolate the marker gene, the total DNA is isolated from the strain *Streptomyces coelicolor* DSM 3030 by cutting with the restriction enzyme BamHI and shotgun cloning into a suitable vector, transformation of a Streptomycetes recipient strain, and selection for production of coloring agent. The positive clones contain an approximately 5.5 kb DNA fragment from DSM 3030.

Figure 2:
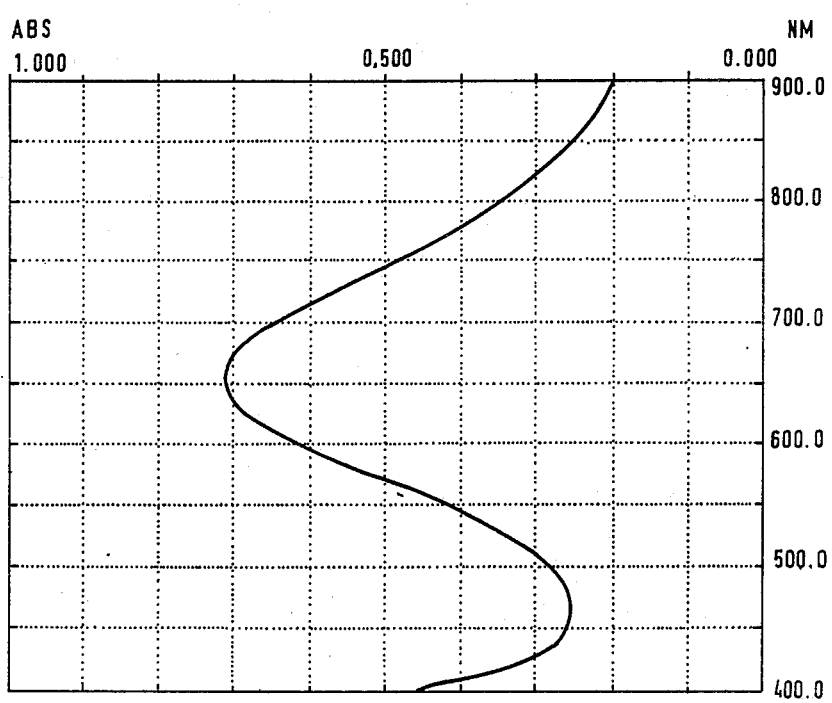

The blue coloring agent which is formed is—in contrast to the water-soluble dyestuff formed in the wild type—insoluble in water but readily dispersible in water. FIG. 2 shows the UV absorption spectrum of an aqueous culture supernatant. The absorption maximum is at 660 nm, and the minimum is at 460 nm. The colonies appear almost black due to a high concentration of coloring agent. In a solid medium the fraction of coloring agent which remains bound to mycelium predominates, and only a small fraction diffuses into the medium. The appearance under the microscope is characteristic: the coloring agent is located in tightly packed spherical bodies on the mycelium and thus makes the colony appear almost black. In liquid culture (tryptic soya broth, "lysis medium A", European patent application with the publication number 0 158 872, page 6) a culture supernatant which is intensely blue in color is obtained after about 3 days. In solid media too, production of the coloring agent takes place irrespective of the medium used ("R2YE" (Hopwood et al., loc. cit.), sporulation medium (German Offenlegungsschrift 3 331 860, Example 1, third medium), "Penassay", "Penassay" with added antibiotics). The blue coloring agent is formed even at the start of growth of the colony and is thus obviously not a product of secondary metabolism.

The 5.5 kb fragment shown in FIG. 1 has a number of cleavage sites suitable for subcloning experiments. It contains no cleavage sites for the enzymes BclI, BglII, HindIII, HpaI, EcoRI, EcoRV and ClaI, and more than 4 cleavage sites for SstII and PvuII.

Suitable host strains for cloning experiments are all Streptomycetes species hitherto investigated, although the amount of coloring agent which is produced may vary not only from species to species but also from strain to strain. However, because of the intensity of the coloration, the marker system according to the invention is also excellently suitable in the strains which show less expression.

Owing to the advantages which have been listed, the marker according to the invention is suitable not only generally for cloning experiments but also specifically for tracing metabolic pathways in Streptomycetes, which are known to be important producers of antibiotics as well as other metabolic products.

The invention is illustrated in detail in the examples which follow. Unless otherwise stated, in these examples percentage data and parts relate to weight.

The figures are true to scale, with the exception of the polylinker regions.

EXAMPLE 1

Preparation of the vector pGM4

Figure 3:
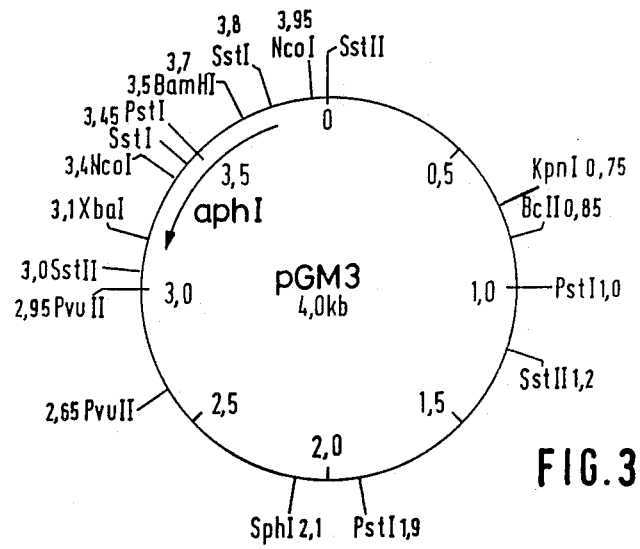

The plasmid pGM1 (European Patent Application with the publication number 0 158 872, FIG. 2) is partially digested with SstII to allow a 3.0 kb fragment to be obtained. The plasmid pSLE16 (European Patent Application with the publication number 0 158 201, FIG. 18) is cut with SstII to allow the 1 kb fragment which contains the neomycin resistance gene aphI to be obtained. Ligation of the two fragments results in the plasmid pGM3 (FIG. 3).

Figure 4:
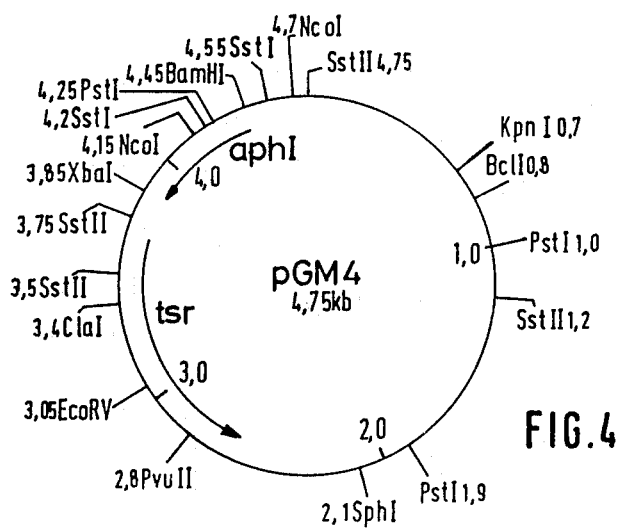

In addition, pSLE41 (European Patent Application No. A2 0 158 201, FIG. 20) is cut with BclI to allow isolation of a 1 kb fragment, whose protruding ends are filled in with Klenow polymerase.

pGM3 is now cut with PvuII, and the 0.3 kb fragment is deleted. The remaining plasmid is now ligated with the BclI fragment which has been made blunt-ended, resulting in the plasmid pGM4 (FIG. 4).

EXAMPLE 2

Preparation of a Gene Bank

*S. coelicolor* DSM 3030 is lysed, and the DNA is isolated in a known manner. The latter is totally digested with BamHI. The plasmid pGM4 (FIG. 4) is cut with BamHI, treated with alkaline phosphatase and ligated with the BamHI fragments. The plasmid population obtained in this way is transformed into the recipient strain *S. lividans* TK 23 (obtainable from the John Innes Foundation). When 1 μg of ligation mixture is used, about 20000 thiostreptone-resistant transformants are obtained, of which 80% are sensitive to neomycin and consequently contain an insert.

EXAMPLE 3

Isolation of the Marker Gene

Transformant colonies with an intense blue-black color were separated off, and the plasmid DNA was isolated from these clones. Subsequent retransformation into *S. lividans* TK 23 produced only colonies with a blue-black color.

Characterization of the plasmid DNA showed that a 5.5 kb BamHI fragment, the characteristics of which are shown in FIG. 1, had been inserted into the aphI gene of pGM4.

This plasmid was called pGM98.

EXAMPLE 4

Transformation of Other Streptomycetes Species

The plasmid pGM98 was transformed into various strains of *S. prasinus* (DSM 40099), *S. viridochromogenes* (DSM 40736=DSM 4112) and *S. ghanaensis* (DSM 2932, ATCC 14672).

The formation of coloring agent was observed in all the strains, but this was somewhat less in *S. prasinus* than in *S. lividans* but somewhat more intense than in *S. ghanaensis*. In no case was plasmid loss observed.

The plasmid pGM98 was also transformed into *S. coelicolor* DSM 3030. In this case formation of coloring agent commenced immediately, whereas in the initial strain (wild type) it is not observed until three days have elapsed. In addition, production of the coloring agent also took place on media on which the wild type forms no blue coloring agent.

DSM 3030 has been deposited at the Deutsche Sammlung von Mikroorganismen und Zellculturen, Mascheroder Weg 1b, D-3300 Braunschweig, West Germany.

We claim:

1. A recombinant DNA comprising a gene coding for a blue coloring agent in Streptomyces, obtainable from the total DNA of *Streptomyces coelicolor* DSM 3030 by cutting with BamHI, cloning a fragment about 5.5 kb in size, and selecting for production of a blue coloring agent.

2. The gene as claimed in claim 1 having restriction sites as set forth in the restriction map of FIG. 1.

3. A plasmid which can amplify in a *Streptomyces* strain, containing as a marker a DNA fragment as defined in claim 1.

4. A plasmid which can amplify in a *Streptomyces* strain, containing as a marker a DNA fragment as defined in claim 2.

5. A plasmid as claimed in claim 3, wherein the marker is an inactivation marker.

6. A plasmid as claimed in claim 4, wherein the marker is an inactivation marker.

* * * * *